US011969576B2

(12) United States Patent
Michaud et al.

(10) Patent No.: US 11,969,576 B2
(45) Date of Patent: Apr. 30, 2024

(54) METHODS OF INCORPORATING CGM DATA INTO DIABETES THERAPY

(71) Applicant: Tandem Diabetes Care, Inc., San Diego, CA (US)

(72) Inventors: Michael Michaud, San Diego, CA (US); Garrett Marin, San Diego, CA (US); Geoffrey A. Kruse, San Diego, CA (US); Jacob Kearns, San Diego, CA (US); Thomas R. Ulrich, Oceanside, CA (US); Trevor Denbo, San Diego, CA (US); David Berger, San Diego, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 640 days.

(21) Appl. No.: 16/920,895

(22) Filed: Jul. 6, 2020

(65) Prior Publication Data
US 2021/0001044 A1 Jan. 7, 2021

Related U.S. Application Data

(60) Provisional application No. 62/870,385, filed on Jul. 3, 2019.

(51) Int. Cl.
*A61M 5/172* (2006.01)

(52) U.S. Cl.
CPC ... *A61M 5/1723* (2013.01); *A61M 2205/3553* (2013.01); *A61M 2205/3569* (2013.01); *A61M 2205/50* (2013.01); *A61M 2205/502* (2013.01); *A61M 2205/505* (2013.01); *A61M 2230/201* (2013.01)

(58) Field of Classification Search
CPC ........ A61M 5/1723; A61M 2205/3553; A61M 2205/3569; A61M 2205/50; A61M 2205/502; A61M 2205/505; A61M 2230/201; A61M 2005/14208; A61M 5/142; A61M 2205/18; A61M 2205/52; A61M 2205/3584; A61M 2205/3592; A61M 2205/056; A61M 5/14244; A61M 2230/005; A61M 2205/702; G16H 20/17; G16H 40/63
See application file for complete search history.

(56) References Cited

U.S. PATENT DOCUMENTS

| | | |
|---|---|---|
| 5,108,363 A | 4/1992 | Tuttle et al. |
| 5,460,605 A | 10/1995 | Tuttle et al. |
| 5,681,285 A | 10/1997 | Ford et al. |
| 6,269,340 B1 | 7/2001 | Ford et al. |

(Continued)

FOREIGN PATENT DOCUMENTS

CA 2930776 C 5/2018

*Primary Examiner* — Dung T Ulsh
(74) *Attorney, Agent, or Firm* — Morgan, Lewis & Bockius LLP

(57) ABSTRACT

Disclosed herein are apparatuses and methods incorporating an infusion pump and a CGM that can include software that automatically populates a blood glucose section of a bolus calculator with a most recent valid CGM value. The software can additionally be programmed to automatically populate the bolus calculator with a single CGM reading only when one or more predefined conditions are met that aid in mitigating the risk of inaccurate and/or invalid single CGM readings.

20 Claims, 7 Drawing Sheets

(56) References Cited

U.S. PATENT DOCUMENTS

| | | |
|---|---|---|
| 6,562,001 B2 | 5/2003 | Lebel et al. |
| 6,571,128 B2 | 5/2003 | Lebel et al. |
| 6,577,899 B2 | 6/2003 | Lebel et al. |
| 6,648,821 B2 | 11/2003 | Lebel et al. |
| 6,668,196 B1 | 12/2003 | Villegas et al. |
| 6,692,456 B1 | 2/2004 | Eppstein et al. |
| 6,740,075 B2 | 5/2004 | Lebel et al. |
| 6,810,290 B2 | 10/2004 | Lebel et al. |
| 6,873,268 B2 | 3/2005 | Lebel et al. |
| 6,958,705 B2 | 10/2005 | Lebel et al. |
| 6,974,437 B2 | 12/2005 | Lebel et al. |
| 7,204,823 B2 | 4/2007 | Estes et al. |
| 7,471,994 B2 | 12/2008 | Ford et al. |
| 7,497,827 B2 | 3/2009 | Brister et al. |
| 7,621,893 B2 | 11/2009 | Moberg et al. |
| 7,651,489 B2 | 1/2010 | Estes et al. |
| 7,678,071 B2 | 3/2010 | Lebel et al. |
| 7,711,402 B2 | 5/2010 | Shults et al. |
| 7,766,873 B2 | 8/2010 | Moberg et al. |
| 7,831,310 B2 | 11/2010 | Lebel et al. |
| 7,837,647 B2 | 11/2010 | Estes et al. |
| 7,998,111 B2 | 8/2011 | Moberg et al. |
| 8,012,119 B2 | 9/2011 | Estes et al. |
| 8,062,257 B2 | 11/2011 | Moberg et al. |
| 8,065,096 B2 | 11/2011 | Moberg et al. |
| 8,182,447 B2 | 5/2012 | Moberg et al. |
| 8,257,300 B2 | 9/2012 | Budiman et al. |
| 8,267,893 B2 | 9/2012 | Moberg et al. |
| 8,287,495 B2 | 10/2012 | Michaud et al. |
| 8,311,749 B2 | 11/2012 | Brauker et al. |
| 8,369,919 B2 | 2/2013 | Kamath et al. |
| 8,573,027 B2 | 11/2013 | Rosinko et al. |
| 8,938,306 B2 | 1/2015 | Lebel |
| 8,986,253 B2 | 3/2015 | DiPerna |
| 9,381,297 B2 | 7/2016 | Brown et al. |
| 9,474,856 B2 | 10/2016 | Blomquist |
| 9,486,171 B2 | 11/2016 | Saint |
| 9,492,608 B2 | 11/2016 | Saint |
| 9,603,995 B2 | 3/2017 | Rosinko et al. |
| 9,669,160 B2 | 6/2017 | Harris |
| 9,737,656 B2 | 8/2017 | Rosinko |
| 9,833,177 B2 | 12/2017 | Blomquist |
| 9,867,937 B2 | 1/2018 | Saint et al. |
| 9,867,953 B2 | 1/2018 | Rosinko |
| 9,940,441 B2 | 4/2018 | Walsh |
| 10,016,561 B2 | 7/2018 | Saint et al. |
| 10,049,768 B2 | 8/2018 | Blomquist |
| 10,052,049 B2 | 8/2018 | Blomquist et al. |
| 10,201,656 B2 | 2/2019 | Rosinko |
| 10,213,547 B2 | 2/2019 | Rosinko |
| 10,279,105 B2 | 5/2019 | Rosinko |
| 10,279,106 B1 | 5/2019 | Cook et al. |
| 10,357,606 B2 | 7/2019 | Rosinko et al. |
| 10,357,607 B2 | 7/2019 | Blomquist et al. |
| 10,463,786 B2 | 11/2019 | Saint |
| 10,478,551 B2 | 11/2019 | Rosinko |
| 10,549,051 B2 | 2/2020 | Rosinko |
| 10,569,016 B2 | 2/2020 | Rosinko |
| 10,780,215 B2 | 9/2020 | Rosinko et al. |
| 10,864,322 B2 | 12/2020 | Saint et al. |
| 10,918,785 B2 | 2/2021 | Rosinko |
| 10,943,687 B2 | 3/2021 | Blomquist |
| 2002/0016568 A1 | 2/2002 | Lebel |
| 2002/0019606 A1 | 2/2002 | Lebel |
| 2002/0065454 A1 | 5/2002 | Lebel |
| 2002/0077852 A1 | 6/2002 | Ford |
| 2003/0055406 A1 | 3/2003 | Lebel |
| 2003/0065308 A1 | 4/2003 | Lebel et al. |
| 2003/0114836 A1 | 6/2003 | Estes |
| 2003/0177041 A1 | 9/2003 | Millica |
| 2003/0225360 A1 | 12/2003 | Eppstein |
| 2004/0193090 A1 | 9/2004 | Lebel et al. |
| 2004/0225252 A1 | 11/2004 | Gillespie et al. |
| 2006/0173444 A1 | 8/2006 | Choy et al. |
| 2007/0287985 A1 | 12/2007 | Estes et al. |
| 2008/0221523 A1 | 9/2008 | Moberg et al. |
| 2008/0228056 A1 | 9/2008 | Blomquist et al. |
| 2009/0192366 A1 | 7/2009 | Mensinger et al. |
| 2009/0192745 A1 | 7/2009 | Kamath et al. |
| 2010/0037680 A1 | 2/2010 | Moberg et al. |
| 2010/0217192 A1 | 8/2010 | Moberg et al. |
| 2010/0217193 A1 | 8/2010 | Moberg et al. |
| 2011/0118699 A1 | 5/2011 | Yodfat et al. |
| 2011/0125095 A1 | 5/2011 | Lebel et al. |
| 2011/0160695 A1 | 6/2011 | Sigrist et al. |
| 2011/0275904 A1 | 11/2011 | Lebel |
| 2012/0041415 A1 | 2/2012 | Estes et al. |
| 2012/0330227 A1 | 12/2012 | Budiman et al. |
| 2013/0053816 A1 | 2/2013 | DiPerna et al. |
| 2013/0324928 A1 | 12/2013 | Kruse |
| 2014/0180203 A1 | 6/2014 | Budiman |
| 2015/0314062 A1 | 11/2015 | Blomquist et al. |
| 2016/0199571 A1 | 7/2016 | Rosinko et al. |
| 2016/0339172 A1 | 11/2016 | Michaud et al. |
| 2017/0000943 A1 | 1/2017 | Blomquist et al. |
| 2017/0049957 A1 | 2/2017 | Michaud |
| 2017/0173261 A1* | 6/2017 | O'Connor ......... A61M 5/14248 |
| 2017/0189614 A1* | 7/2017 | Mazlish .............. A61M 5/1452 |
| 2017/0199985 A1* | 7/2017 | Mazlish ............ A61M 5/14244 |
| 2017/0348484 A1* | 12/2017 | Duke .................... G16H 50/30 |
| 2018/0092578 A1 | 4/2018 | Blomquist |
| 2018/0133397 A1 | 5/2018 | Estes |
| 2018/0133398 A1 | 5/2018 | Blomquist |
| 2018/0161498 A1 | 6/2018 | Estes |
| 2018/0177946 A1* | 6/2018 | Loutseiko ........... A61M 5/1723 |
| 2018/0226145 A1 | 8/2018 | Walsh |
| 2018/0233221 A1 | 8/2018 | Blomquist |
| 2018/0361060 A9 | 12/2018 | Rosinko |
| 2019/0167901 A1 | 6/2019 | Rosinko |
| 2019/0321545 A1 | 10/2019 | Saint |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0016335 A1 | 1/2020 | DiPerna et al. |
| 2020/0086043 A1 | 3/2020 | Saint |
| 2020/0101226 A1 | 4/2020 | Saint et al. |
| 2020/0114076 A1 | 4/2020 | Ulrich et al. |
| 2020/0171249 A1 | 6/2020 | Rosinko |
| 2020/0179603 A1 | 6/2020 | Rosinko |
| 2020/0197605 A1* | 6/2020 | Haidar ................. G05B 13/048 |
| 2020/0254174 A1 | 8/2020 | Kruse et al. |
| 2020/0261649 A1 | 8/2020 | Michaud |
| 2020/0368430 A1 | 11/2020 | Ulrich et al. |

* cited by examiner

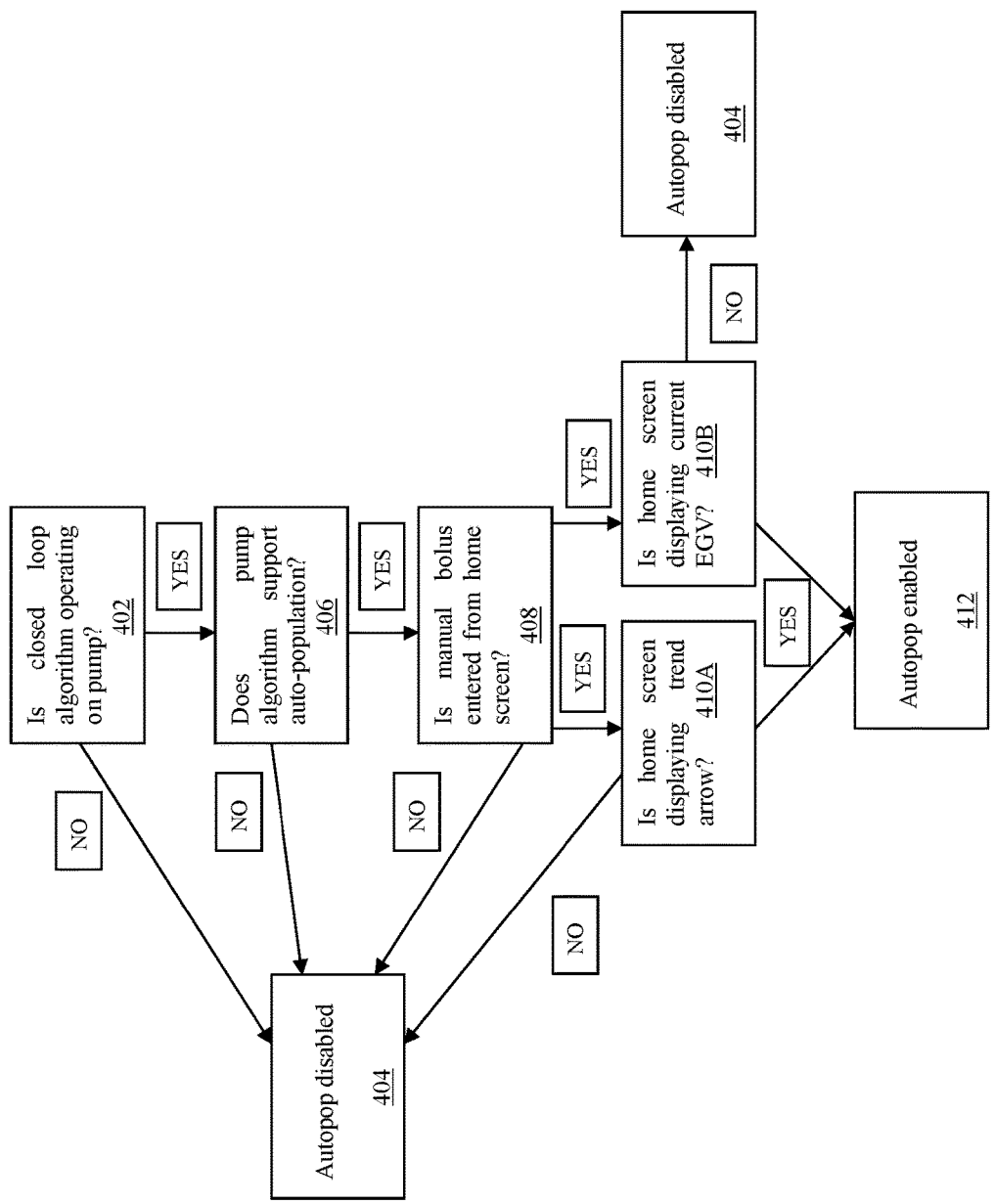

METHODS OF INCORPORATING CGM DATA INTO DIABETES THERAPY

RELATED APPLICATION

The present application claims the benefit of U.S. Provisional Application No. 62/870,385 filed Jul. 3, 2019, which is hereby incorporated herein in its entirety by reference.

FIELD OF THE INVENTION

The present invention relates generally to ambulatory infusion pumps and, more particularly, to the operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring (CGM) devices. A CGM device consists of a sensor placed under the patient's skin and affixed to the patient via an adhesive patch, a transmitter, and a monitor. A CGM device samples the patient's interstitial fluid periodically (e.g. once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because these systems serve to mimic biological functions of the pancreas for persons with diabetes.

The delivery of insulin pump therapy based on CGM readings necessitates accurate and reliable CGM data output. Some CGM devices are calibrated with blood samples to correlate actual blood glucose data with the CGM readings. These calibrations are only done periodically, such as every few days or hours (e.g., 12 hours). The longer it has been since a calibration event, the more likely the CGM data is unreliable to some degree and the more unreliable the CGM data is likely to become until the next calibration. In addition, any malfunction of the CGM sensor, loss of signal or communication with the CGM, etc., will necessarily exclude lost CGM readings from the algorithm(s) calculating pump therapy doses. For these reasons, a need exists for additional safety features in AID systems when CGM readings may be less accurate or reliable as a proxy for a user's blood glucose levels.

SUMMARY

Disclosed herein are systems and methods incorporating an ambulatory infusion pump and a CGM. These systems that can include software and related methods to automatically populate certain fields of a bolus calculator with a most recent CGM reading only when one more predefined conditions are met. These predefined conditions, used alone or any combination with one another, aid in mitigating the risk that an inaccurate, unreliable, or invalid CGM reading will adversely impact insulin delivery to a user.

In an embodiment, an ambulatory infusion pump system can include a pump mechanism configured to facilitate delivery of insulin to a user, a user interface, a communications device adapted to receive glucose levels from a continuous glucose monitor and a processor functionally linked to the pump mechanism, the user interface and the communications device. The processor can be configured to automatically calculate insulin doses with a closed loop delivery algorithm based on glucose levels received from the continuous glucose monitor and deliver the calculated insulin doses to the user with the pump mechanism. The processor can further display a bolus programming feature for programming a bolus delivery of insulin to the user. The processor can then determine whether the closed loop delivery algorithm supports an auto-population feature, whether the bolus programming feature was manually accessed by the user and whether the glucose levels received from the continuous glucose monitor are valid. The auto-population feature can be activated to automatically populate a blood glucose field in the bolus programming feature with a most recent glucose level received from the continuous glucose monitor only if the closed loop delivery algorithm supports the auto-population feature, the bolus programming feature was manually accessed by the user and the glucose levels received from the continuous glucose monitor are valid.

In an embodiment, an ambulatory infusion pump system can include a pump mechanism configured to facilitate delivery of insulin to a user, a user interface, a communications device adapted to receive glucose levels from a continuous glucose monitor and a processor functionally linked to the pump mechanism, the user interface and the communications device. The processor can be configured to automatically calculate insulin doses with a closed loop delivery algorithm based on glucose levels received from the continuous glucose monitor and deliver the calculated insulin doses to the user with the pump mechanism. The processor can further display a bolus programming feature for programming a bolus delivery of insulin to the user. The processor can then execute an auto-population risk mitigation procedure required to automatically populate a most recent glucose level received from the continuous glucose monitor into a blood glucose field of the bolus programming feature. The risk mitigation procedure can require verification of one or more predefined conditions that aid in mitigating the risk of an inaccurate or invalid most recent glucose level. The processor can automatically populate the blood glucose field in the bolus programming feature with the most recent glucose level received from the continuous glucose monitor only if the auto-population risk mitigation procedure verifies the one or more predefined conditions.

The features described in the present disclosure can be used individually or together in any number of combinations to auto-populate CGM data while addressing such risk to provide a system that decreases user errors and increases user convenience with the automatically populated CGM data while also mitigating accuracy and reliability challenges for single point CGM readings.

BRIEF DESCRIPTION OF THE DRAWINGS

The invention may be more completely understood in consideration of the following detailed description of various embodiments of the invention in connection with the accompanying drawings, in which:

FIG. 7 depicts a flowchart of steps for enabling an auto-population feature according to the disclosure.

Figure 1:
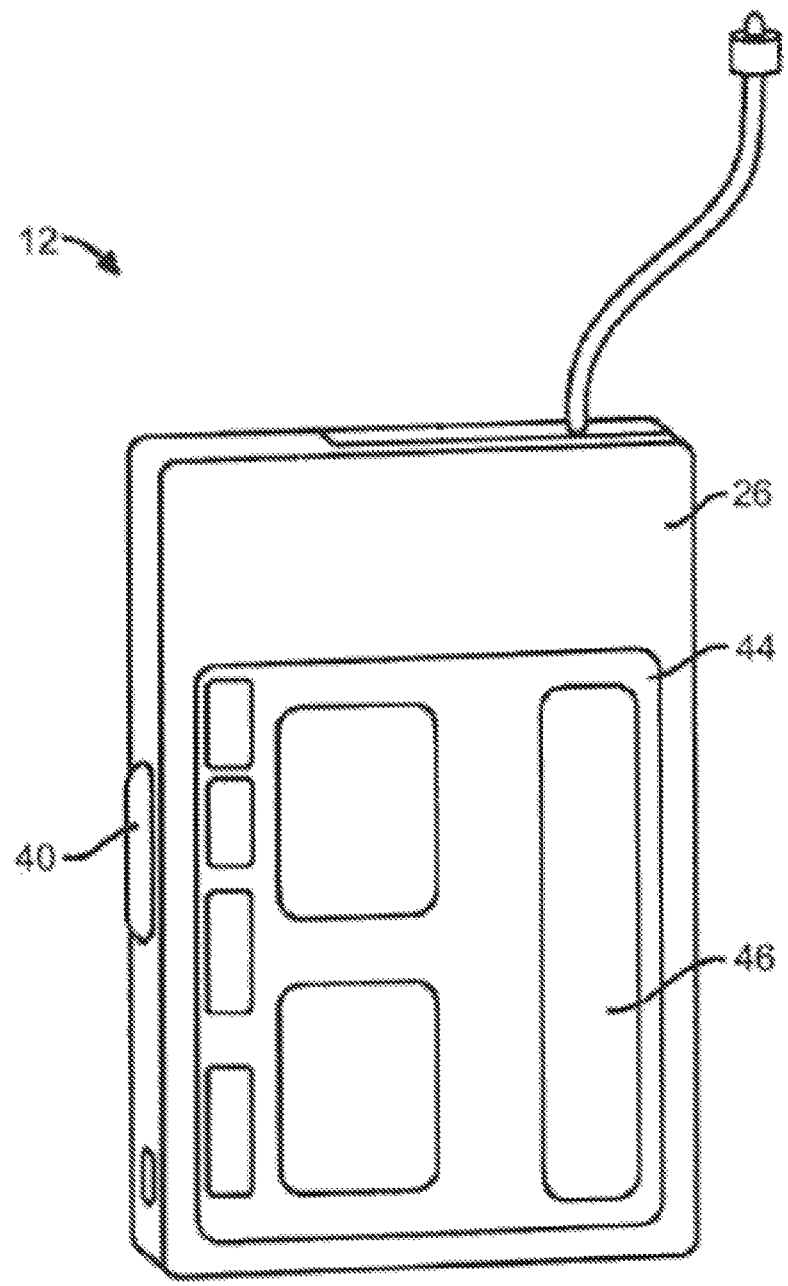
FIG. 1 is an embodiment of an ambulatory infusion pump for use with embodiments of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
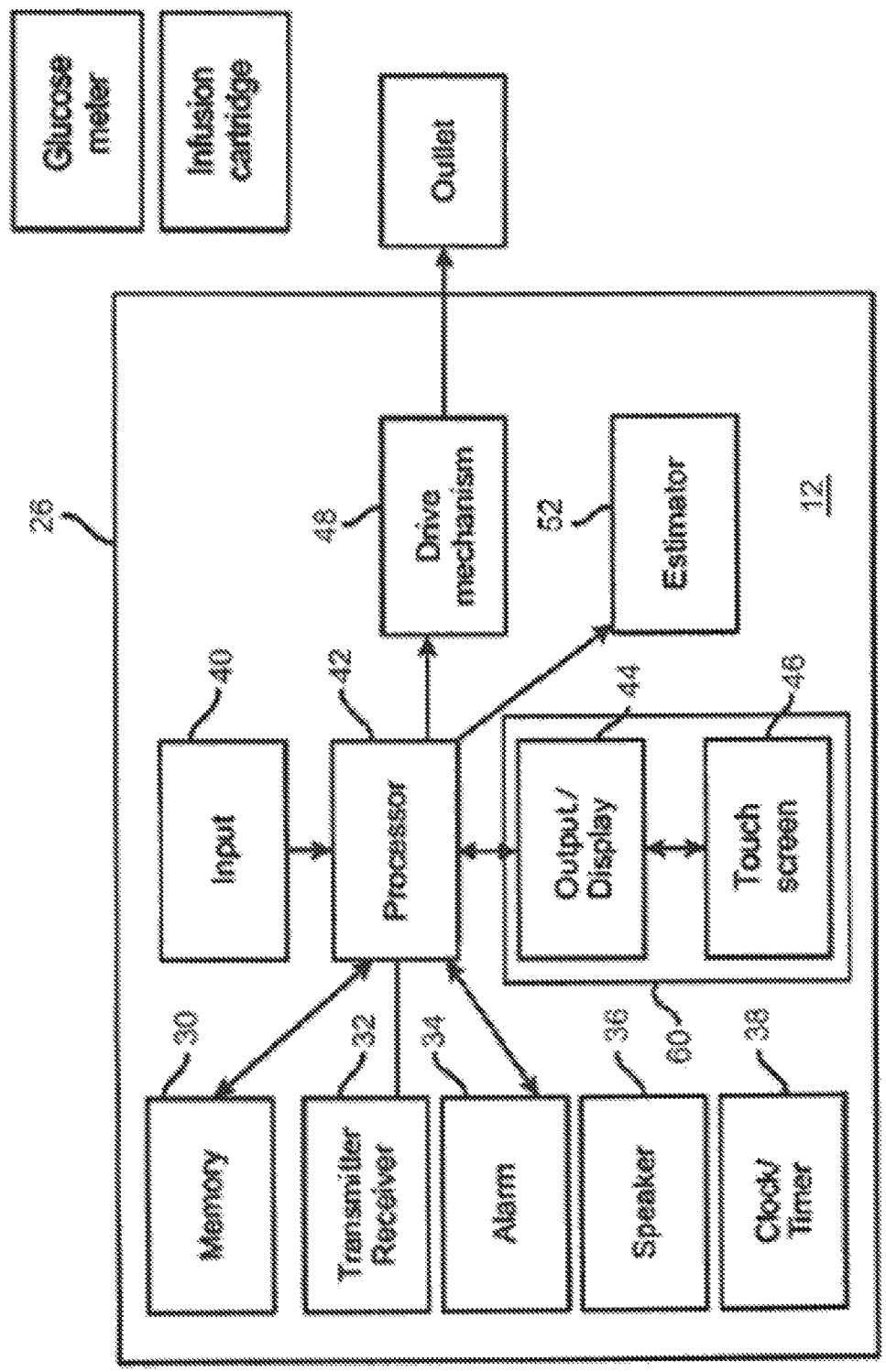
FIG. 2 is a block diagram of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, or the like.

Figure 3A:
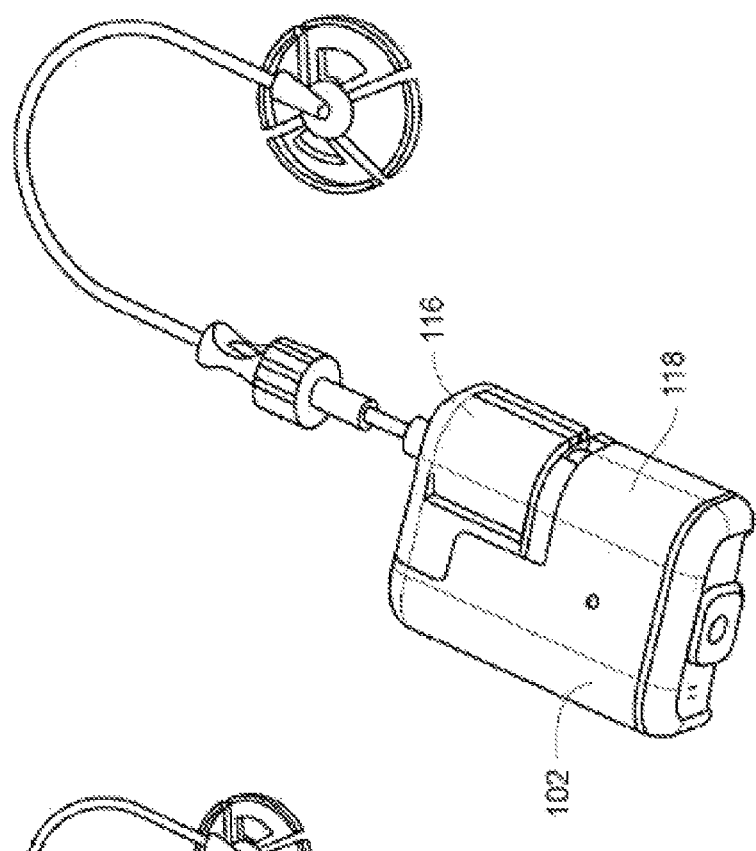
FIGS. 3A-3B are an alternate embodiment of an ambulatory infusion pump for use with embodiments of the disclosure.
Figure 3B:
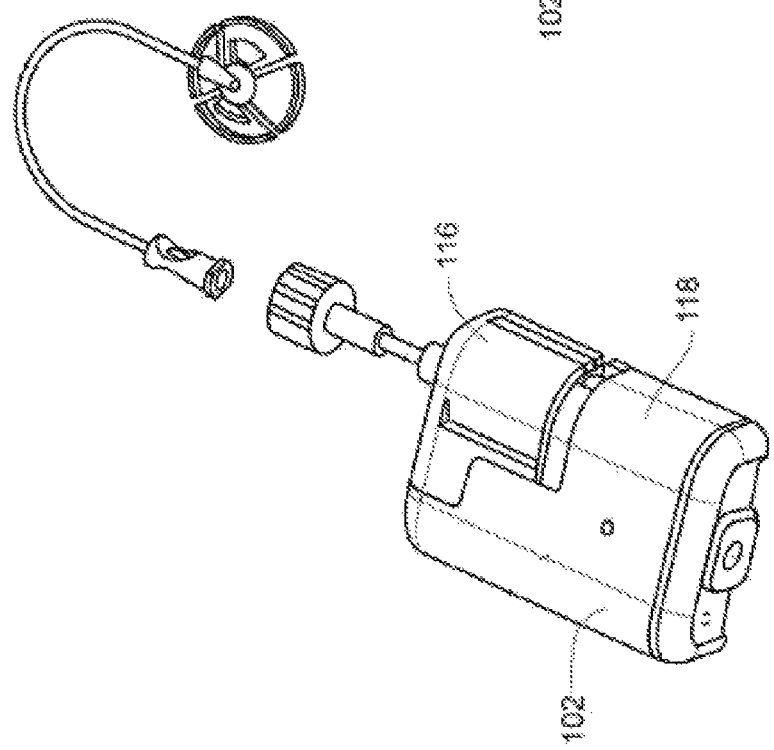

FIGS. 3A-3B depicts a second infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
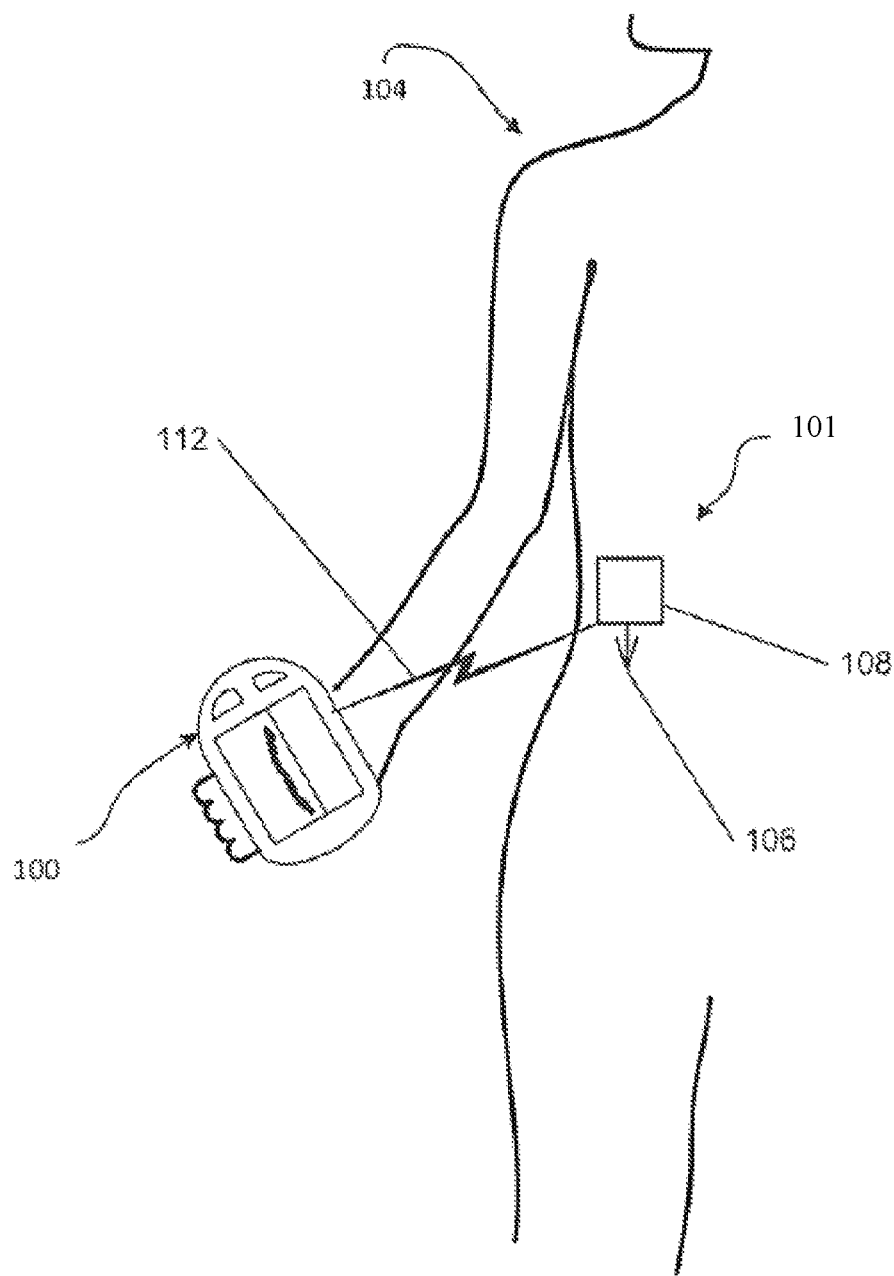
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). The sensor 101 is removably affixed to a user 104 and includes a sensor probe 106 configured for transcutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level (hyperglycemia), the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus, but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence. Such determination can be made by the infusion pump providing therapy or by a separate device that transmits therapy parameters to the infusion pump. In some embodiments, multiple medicaments can be employed in such an ambulatory infusion system as, for example, a first medicament, e.g., insulin, that lowers blood glucose levels and a second medicament, e.g., glucagon, that raises blood glucose levels.

Figure 5:
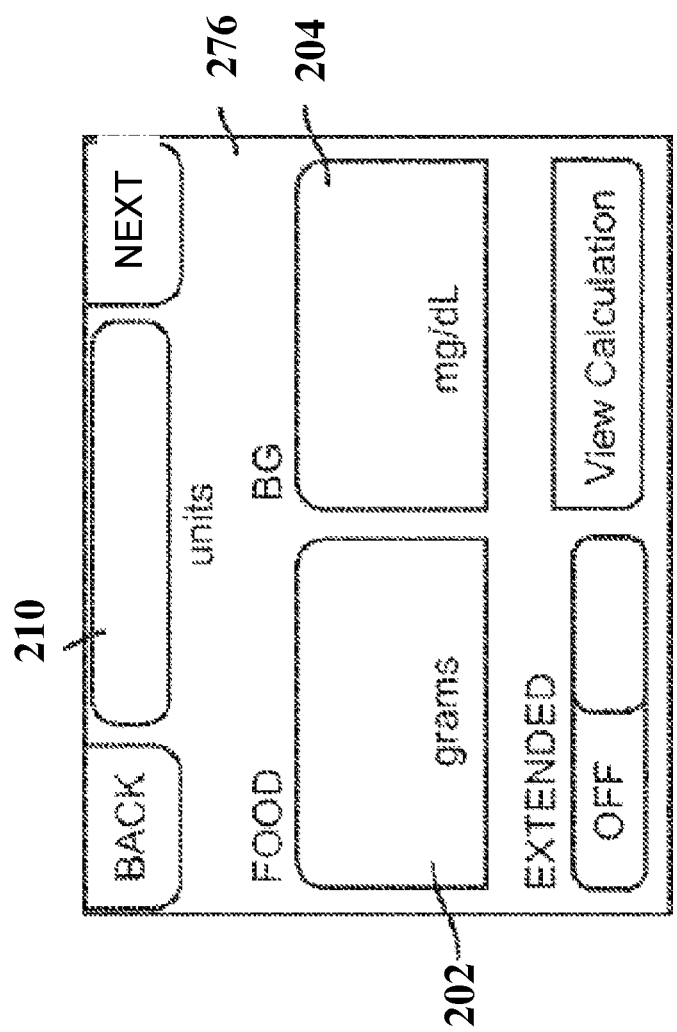
FIG. 5 depicts an embodiment of a bolus calculator according to the disclosure.

A user may require or desire a bolus dose of medicament from his/her pump for a number of reasons including, for example, food ingestion, a high blood glucose and/or CGM reading, an increasing CGM trend, an increasing CGM trend and a high CGM reading, and other symptoms indicating that BG is increasing or already high. Typically, to receive a bolus dose, the user must manually enter numerical inputs into a bolus programming feature (e.g., a bolus setup page or calculator) presented on an infusion pump and/or a remote controller device. FIG. 5 depicts an example bolus calculator 276. Bolus calculator 276 can include a FOOD BOLUS object 202 and a BLOOD GLUCOSE (BG) object 204. The FOOD BOLUS object 202 is selectable to enable a user to enter a number of grams of carbohydrates consumed or intended to consume. If a user is consuming a meal with multiple food items, he or she will need to add the separate carbohydrate values together and enter the total carbohydrate value of the meal to calculate a bolus. The setup page 276 can then display both the amount of carbohydrates entered into the FOOD BOLUS object 202 and the units of insulin calculated by the device for delivery—based on the entered carbohydrate amount and a stored insulin sensitivity factor—in a UNITS object 210. An ADD BG object 204 can alternatively or additionally be selected to enable the device to calculate whether a correction bolus should be delivered based on a blood glucose level of the user entered via the ADD BG object 204.

The bolus calculator of FIG. 5 calculates a correction bolus based on an entry into the ADD BG object 204 based on the following equations:

(Current Glucose Value−Target Glucose Value)/Insulin Sensitivity Factor=Correction Insulin Correction Insulin−Insulin On Board=Correction Bolus If the correction bolus is a positive value, the pump may deliver the calculated correction bolus. If the correction bolus result is a negative value, the pump may apply a reverse correction and remove insulin from the correction bolus. This is most applicable at mealtimes when the reverse correction decreases the total meal bolus administered for the meal.

In addition to the user inconvenience of having manually input information into the ambulatory infusion pump system, the above approach is susceptible to user errors including error in transcribing data into the ADD BG object 204 from one location (e.g., a CGM) to another (e.g, to the GUI 60 on the pump 12 or the remote control device). If a user inadvertently inputs the wrong information into the bolus calculator (e.g., entering a reading of 40 mg/dL instead of 400 mg/dL), an incorrect amount of insulin can be instructed to be delivered as part of the correction bolus leading to potentially undesirable consequences. Such potential errors can be avoided by utilizing the CGM data to automatically populate the ADD BG object 204 or other data entry field in a bolus calculator with the most recent CGM reading.

Figure 6:
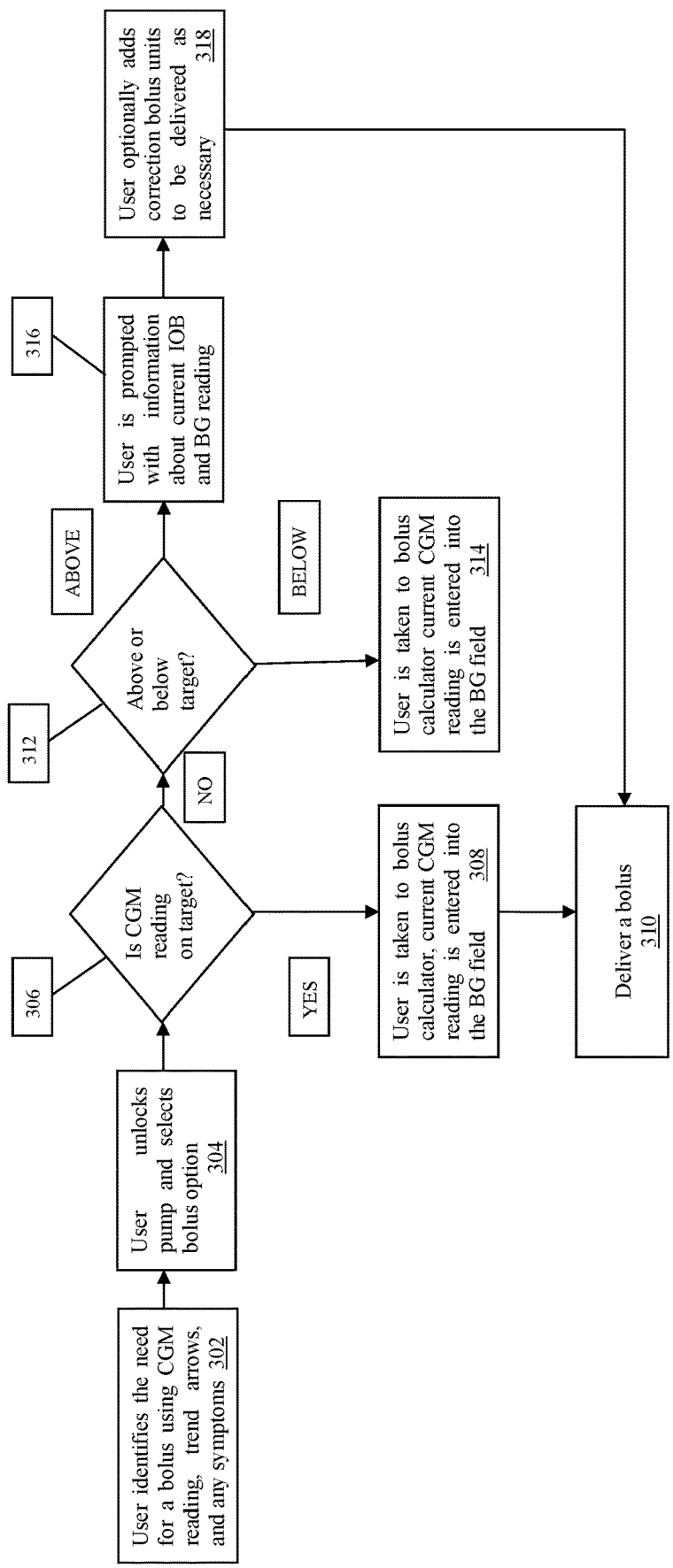
FIG. 6 depicts a flowchart of steps for programming a bolus according to the disclosure.

According to a broad aspect of the present disclosure, a system incorporating an infusion pump and a CGM as described herein can include software that automatically populates the BG section of the bolus calculator with the most recent valid CGM reading. The auto-populate feature can proceed as depicted in FIG. 6. When the user identifies a need for a bolus, based on, for example, a CGM reading, CGM trend arrow, a meal, other symptoms, etc. at step 302, the user can unlock the pump and access a bolus function through, e.g., a bolus button, a bolus menu item or icon, etc. at step 304. When the bolus calculator is accessed, at step 306 the system determines if the most recent CGM reading is on target (e.g., equal to or within a threshold amount of a target glucose level). If the reading is on target, at step 308 the user is presented with the bolus calculator with the current CGM reading in the BG field. The user can then program a meal bolus as needed to be delivered at step 310, with the system taking into account the CGM reading in calculating insulin to be delivered for the meal as noted above. If the reading is not on target, at step 312 the system then determines if the reading is above or below the target. If the reading is below the target, the user is taken to the bolus calculator with the CGM reading auto-populated in the BG field at step 314. In some embodiments, the user can still deliver a meal bolus taking into account the below target CGM reading, as described above. If the reading is above the target, the user can be prompted with information about the user's current insulin-on-board and a measured BG level at step 316. The user can then optionally add additional correction bolus units as necessary based on the information at step 318 for a bolus that is delivered at step 310. In some embodiments, when the reading is above the target the user can be taken to the bolus calculator with the CGM reading auto-populated before and/or after the prompt for additional information. In other embodiments, the bolus can be calculated and delivered without displaying the bolus calculator. Alternatively, the user can be taken directly to the bolus calculator with an above target reading auto-populated and the bolus delivered without prompting for additional information.

As discussed above, use of CGM readings to determine therapy requires reliable and accurate CGM data. Because the automatic bolus feature described above with respect to FIG. 6 uses a single CGM reading, at times it is possible that the CGM reading may not be accurate or reliable.

According to another broad aspect of the present disclosure, the software can additionally be programmed to execute a risk mitigation procedure that automatically populates the bolus calculator with a single CGM reading only when one or more predefined conditions are met. As will be described in greater detail below, the present disclosure includes a number of optional features that may be used individually or together in any number of combinations to automatically populate CGM readings into the bolus calculator in such a way that mitigates the possibility that an inaccurate, unreliable, or otherwise invalid single CGM reading could adversely impact the bolus dose to the user.

In a first embodiment, four conditions must be met for the system to enable the auto-populate feature for the bolus condition. A first condition is that the CGM reading is between 40 mg/dL and 400 mg/dL, as a reading outside of the range indicates that the CGM data is unreliable and the CGM likely needs to be recalibrated. A second condition is that the CGM reading is valid, with no error codes or invalid information sent from the CGM transmitter. The third condition is that a valid CGM trend (which in some systems may be indicated with an arrow), is available, e.g., increasing or decreasing glucose levels, indicating that a number of valid readings have been received over a recent time period. If these conditions are not met, the system may disable the auto-populate feature.

Certain ranges of blood glucose levels are known to adversely impact CGM accuracy. For example, data derived from an in silico model of Type I diabetes indicates that higher CGM readings (i.e., over 250 mg/dL) increase the likelihood of hypoglycemia. In a second embodiment, the system may disable the auto-populate feature unless one or more of the following conditions are met: 1) the current CGM reading is less than a high threshold such as 250 mg/dL; 2) the CGM rate of change (ROC) is increasing at less than a defined threshold rate such as 2 mg/DL; and 3) the CGM ROC is decreasing at less than a defined threshold rate such as 2 mg/DL. In embodiments, the increasing and decreasing ROC thresholds could be the same or different values.

As noted above, infusion pumps can operate in closed-loop or semi-closed loop modes to automatically deliver medicament based on CGM data. To operate in such modes, the pump may require multiple valid CGM readings and trend data, which mitigates the likelihood that the single data point used to populate the bolus calculator is inaccurate, unreliable, or otherwise invalid. In a third embodiment, the auto-populate feature can be disabled unless the pump is in semi-closed-loop mode and/or closed-loop mode due to the inherent risk mitigation provided by the requirements to operate in these delivery modes.

CGM Low Alerts are alerts issued when the CGM detects that the glucose level is or is going low that have been clinical proven to be highly accurate and an effective indicator of pending hypoglycemia. In some systems, multiple valid CGM readings and trend data are required for the feature to operate. In a fourth embodiment, the auto-populate feature can be disabled unless a CGM Low Alert Feature is activated. This similarly mitigates the risk of not having a reliable, accurate, and/or valid CGM data point.

In a fifth embodiment, this feature related to a CGM Low Alert can be combined with the above-described embodiment relating to a requirement for the pump to be in closed-loop mode and/or semi-closed-loop mode.

In a sixth embodiment, a user may be able to enter a bolus target BG within a certain range in a bolus profile, such as, for example, between 70 mg/dL and 250 mg/dL. As noted above, certain CGM ranges are known to have higher or lower accuracy. In embodiments, if the programmed target is greater than and/or equal to a target BG within a more accurate CGM range (e.g., greater than or equal to 120 mg/DL), then the system can enable the auto-populate feature using CGM data. If the target BG is below and/or outside of the more accurate CGM range, i.e., in a range in which in silico modeling has shown there is a greater likelihood of hypoglycemia, the system can disable the auto-populate feature.

In a seventh embodiment, when the auto-populate feature is enabled, the system may temporarily, automatically, and/or selectively set a higher BG target for a correction bolus. For example, the system can set a BG target 10-20% higher than the stored BG target input by the user or otherwise programmed into the device. This feature can aid in mitigating the risk of inadvertently dosing too much medicament such as insulin based on an invalid CGM reading by reducing the amount and/or frequency of dosing with the auto-populate feature.

In an eighth embodiment, the system can operate with the auto-populate feature enabled, but temporarily, automatically, and/or selectively dose less than the calculated correction bolus amount when the auto-populate feature is employed. For example, the system can deliver 80% or some other reduced value of the calculated correction bolus. This can also aid in mitigating the risk of inadvertently dosing too much medicament such as insulin based on an invalid CGM reading by reducing the amount of dosing with the auto-populate feature.

In a ninth embodiment, the system can enable the auto-populate feature only if the type, brand, etc. of CGM being utilized by the system at a given time meets a certain accuracy and/or reliability criteria. In some embodiments, the system can store one or more lists of approved and/or disapproved CGM devices for which the auto-populate feature can be enabled or disabled, respectively.

In a tenth embodiment, the system can enable the auto-populate feature, but set a global threshold limit on bolus size (e.g., a limit on the size of a meal bolus, correction bolus, or the like) when using the auto-populate feature. In some embodiments, the user may be prohibited from delivering a bolus greater than the threshold. In other embodiments, if the user attempts to deliver a bolus greater than the threshold, the user can be directed to a secondary confirmation step. The secondary confirmation can include, for example, one or more of a requirement to manually check and input a BG value, a waiting period for multiple valid CGM readings, or the like.

In an eleventh embodiment, the system can enable the auto-populate feature, but only allow a meal bolus to be programmed into the bolus calculator while the auto-populate feature is enabled instead of other correction boluses not based on the auto-populate feature.

In a twelfth embodiment, the system can be configured to enable the auto-populate feature only if there has been a recent finger stick calibration within a predetermined period of time and/or if the most recent calibration shows no significant deviation between the estimated CGM glucose level and the measured BG level. This mitigates risk because the recent calibration provides a higher likelihood of an accurate and reliable CGM data point.

In a thirteenth embodiment, the system may enable the auto-populate feature only during certain times of the day. For example, the system can disable the feature an hour before a typical and/or programmed bedtime to mitigate the risk of the user giving a correction bolus based on an invalid CGM reading right before bedtime when the user will not be eating and/or active enough to use the extra insulin.

In a fourteenth embodiment, the system can be programmed to include a Warning, Check BG instruction after a bolus if, after giving a correction bolus in auto-populate mode, communication with the CGM is out of range and/or an operating semi-closed-loop mode or closed-loop mode is disabled within a predetermined time following the bolus delivery (e.g., 15 minutes). Such an embodiment can optionally be used in conjunction with the embodiment described above that only enables the auto-populate feature when a semi-closed-loop mode or closed-loop mode is active.

Referring now to FIG. 7, a flowchart of steps taken by an ambulatory infusion pump system in order to enable an auto-populate feature as described herein is depicted. At step 402 the system initially determines whether or not there is a closed loop algorithm automatically determining at least some decisions based on CGM data operating on the pump. If not, the auto-population feature is not enabled. This requirement can be included in some embodiments because the fact that a closed loop algorithm is running indicates that the system has been receiving CGM data. If a closed loop algorithm is not operating, auto-population is disabled at step 404. If a closed loop algorithm is running, at step 406 the system determines whether or not the closed loop algorithm making therapy determinations for the pump using CGM data is an algorithm that supports auto-population, as not all algorithms may be programmed to be able to use auto-population. If the algorithm does not support auto-population, at step 404 auto-population is not enabled.

Still referring to FIG. 7, if the closed loop algorithm operating on the system is an algorithm that supports auto-population, the system then determines if the bolus calculator was accessed by selection of a manual bolus option from a device menu or screen such as the home screen at step 408. This is because auto-population may in some embodiments only be applicable to entering the bolus programming feature through a manual bolus rather than through other means such as a preset additional bolus reminder, a bolus after CGM calibration, etc. If the manual bolus feature has been selected, the system then determines whether or not the home screen is displaying a CGM trend arrow at step 410A and a current estimated glucose value at step 410B. These steps are carried out due to restrictions on using CGM values to make dosing decisions to ensure that the pump has been receiving both a recent CGM value as well as enough consecutive valid CGM values to be able to identify a trend. If the home screen was displaying both indicators, then auto-population is enabled at step 412 and the most recent single CGM value can be automatically entered into the CGM calculator. Bolus programming and delivery can then proceed as set forth above.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; and 10,569,016. commonly owned U.S. Patent Publication Nos. 2009/0287180; 2012/0123230; 2013/0053816; 2014/0276423; 2014/0276569; 2014/0276570; 2018/0021514; 2018/0071454; 2019/0240398; 2019/0307952; 2019/0365997 and 2020/0114076 and commonly owned U.S. patent application Ser. Nos. 16/507,146; 16/725,278; 16/725,337; 16/793,662; 16/830,415; 16/879,363; and Ser. No. 16/879,927.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
a pump mechanism configured to facilitate delivery of insulin to a user;
a user interface;
a communications device adapted to receive glucose levels from a continuous glucose monitor;
a processor functionally linked to the pump mechanism, the user interface and the communications device, the processor configured to:
automatically calculate insulin doses with a closed loop delivery algorithm based on glucose levels received from the continuous glucose monitor;
deliver the calculated insulin doses to the user with the pump mechanism;
display a bolus programming feature for programming a bolus delivery of insulin to the user;
determine whether the closed loop delivery algorithm supports an auto-population feature;
determine whether a current glucose level received from the continuous glucose monitor is valid; and
activate the auto-population feature to automatically populate a blood glucose field in the bolus programming feature with a most recent glucose level received from the continuous glucose monitor only if the closed loop delivery algorithm supports the auto-population feature, the current glucose level received from the continuous glucose monitor is valid, and a rate of change of glucose levels received from the continuous glucose monitor satisfies a certain defined threshold.

2. The system of claim 1, wherein determining whether the glucose levels received from the continuous glucose monitor are valid includes determining whether one or more icons relating to the glucose levels were displayed on the user interface when the bolus programming feature was displayed.

3. The system of claim 2, wherein the one or more icons include a current glucose level.

4. The system of claim 2, wherein the one or more icons include a trend arrow providing an indication of a glucose trend based on a series of glucose values from the continuous glucose monitor.

5. The system of claim 2, wherein determining whether the one or more icons relating to the glucose levels were displayed on the user interface incudes determining whether the one or more icons were displayed on a home screen of the user interface.

6. The system of claim 1, wherein the processor is further configured to compare the most recent glucose level from the continuous glucose monitor automatically populated into the blood glucose field in the bolus programming feature to a target glucose level.

7. The system of claim 6, wherein if the most recent glucose level is below the target glucose level, a meal bolus programmed with the bolus programming feature is reduced based on a difference between the target glucose level and the most recent glucose level.

8. The system of claim 6, wherein if the most recent glucose level is above the target glucose level, a meal bolus programmed with the bolus programming feature is increased based on a difference between the most recent glucose level and the target glucose level.

9. The system of claim 1, wherein the user interface is part of an ambulatory infusion pump that includes the pump mechanism.

10. The system of claim 1, wherein the user interface is part of a remote control device for remotely controlling an ambulatory infusion pump that includes the pump mechanism.

11. An ambulatory infusion pump system, comprising:
a pump mechanism configured to facilitate delivery of insulin to a user;
a user interface;

a communications device adapted to receive glucose levels from a continuous glucose monitor;

a processor functionally linked to the pump mechanism, the user interface and the communications device, the processor configured to:

automatically calculate insulin doses with a closed loop delivery algorithm based on glucose levels received from the continuous glucose monitor;

deliver the calculated insulin doses to the user with the pump mechanism;

display a bolus programming feature for programming a bolus delivery of insulin to the user;

execute an auto-population risk mitigation procedure required to automatically populate a most recent glucose level received from the continuous glucose monitor into a blood glucose field of the bolus programming feature, the risk mitigation procedure requiring verification of one or more predefined conditions that aid in mitigating the risk of an inaccurate or invalid most recent glucose level; and automatically populate the blood glucose field in the bolus programming feature with the most recent glucose level received from the continuous glucose monitor only if the auto-population risk mitigation procedure verifies the one or more predefined conditions including whether a rate of change of glucose levels received from the continuous glucose monitor satisfies a certain defined threshold.

12. The system of claim 11, wherein the one or more predefined conditions include that the closed loop delivery algorithm supports the auto-population feature.

13. The system of claim 11, wherein the one or more predefined conditions include that the bolus programming feature was manually accessed by the user.

14. The system of claim 11, wherein the one or more predefined conditions include that recent glucose levels received from the continuous glucose monitor are valid.

15. The system of claim 14, wherein verifying that the glucose levels received from the continuous glucose monitor are valid includes determining whether one or more icons relating to the glucose levels were displayed on the user interface when the bolus programming feature was displayed.

16. The system of claim 15, wherein the one or more icons include a current glucose level.

17. The system of claim 15, wherein the one or more icons include a trend arrow providing an indication of a glucose trend based on a series of glucose values from the continuous glucose monitor.

18. The system of claim 1, wherein the processor is further configured to compare the most recent glucose level from the continuous glucose monitor automatically populated into the blood glucose field in the bolus programming feature to a target glucose level.

19. The system of claim 18, wherein if the most recent glucose level is below the target glucose level, a meal bolus programmed with the bolus programming feature is reduced based on a difference between the target glucose level and the most recent glucose level.

20. The system of claim 18, wherein if the most recent glucose level is above the target glucose level, a meal bolus programmed with the bolus programming feature is increased based on a difference between the most recent glucose level and the target glucose level.

* * * * *